United States Patent [19]
Peluso et al.

[11] Patent Number: 5,697,900
[45] Date of Patent: Dec. 16, 1997

[54] SOLUTION DELIVERY SYSTEM WITH INDIVIDUAL INTEGRATED FINAL PACKAGING AND A METHOD FOR PACKAGING THE SAME

[75] Inventors: Francesco Peluso, Heverlee; Patrick R. Balteau, Jambes; Eric J. Hénaut, Arquennes, all of Belgium

[73] Assignee: Baxter International Inc., Deerfield, Ill.

[21] Appl. No.: 657,832

[22] Filed: May 31, 1996

[51] Int. Cl.⁶ .................................................. A61M 1/00
[52] U.S. Cl. .................... 604/28; 604/29; 604/259; 604/260; 206/438
[58] Field of Search .............................. 604/28, 29, 257, 604/258, 259, 260, 903; 206/438

[56] References Cited

U.S. PATENT DOCUMENTS 4,326,526  4/1982  Buck et al. ................................ 604/29
4,585,436  4/1986  Davis et al. .............................. 604/29

*Primary Examiner*—Michael Buiz
*Assistant Examiner*—Julian W. Woo
*Attorney, Agent, or Firm*—Thomas S. Borecki; Charles R. Mattenson; Robert M. Barrett

[57] ABSTRACT

A system and a method are provided for packaging components required for conducting a dialysis procedure. To this end, a rigid container is designed such that other necessary components required for conducting a dialysis procedure may be contained therein prior to use. The rigid container is designed with a lid having a port in the lid such that a drainage line may be connected to the port and the rigid container may be used as a drainage container. The rigid container is constructed from a rigid material such that rigid containers may be stacked during transport and storage of the same. The rigid container may also be re-used for subsequent dialysis procedures.

27 Claims, 2 Drawing Sheets

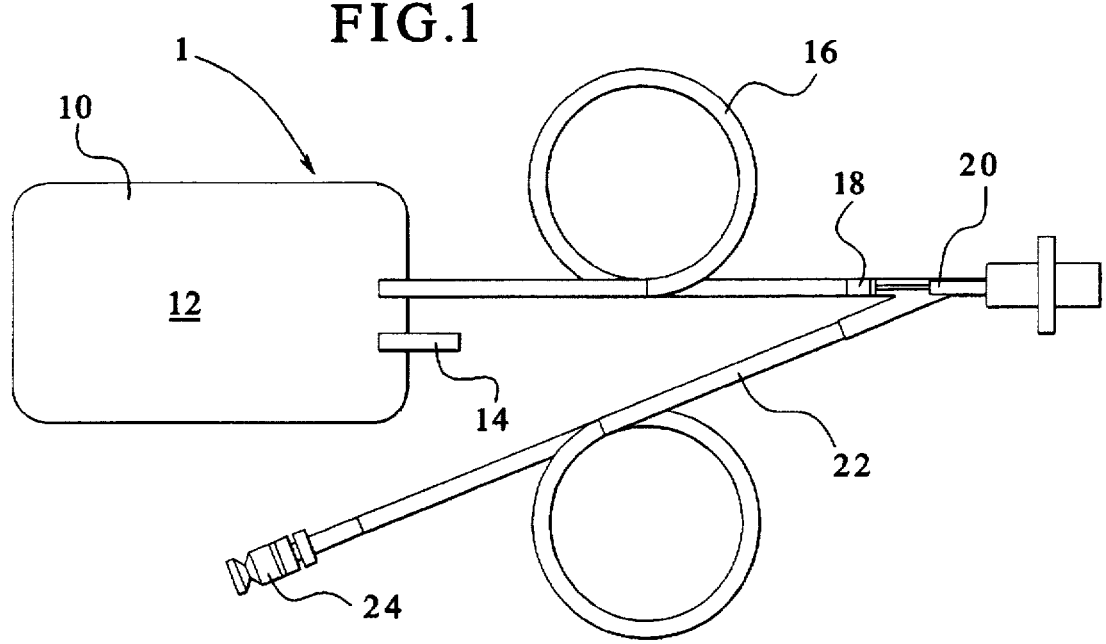
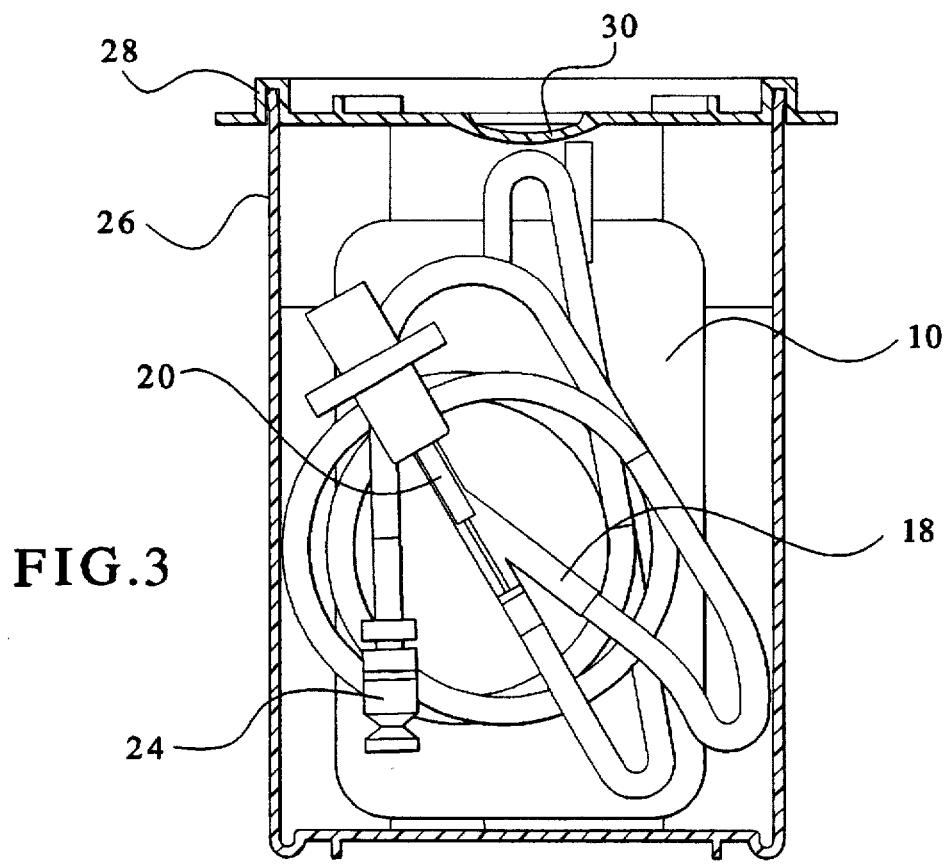

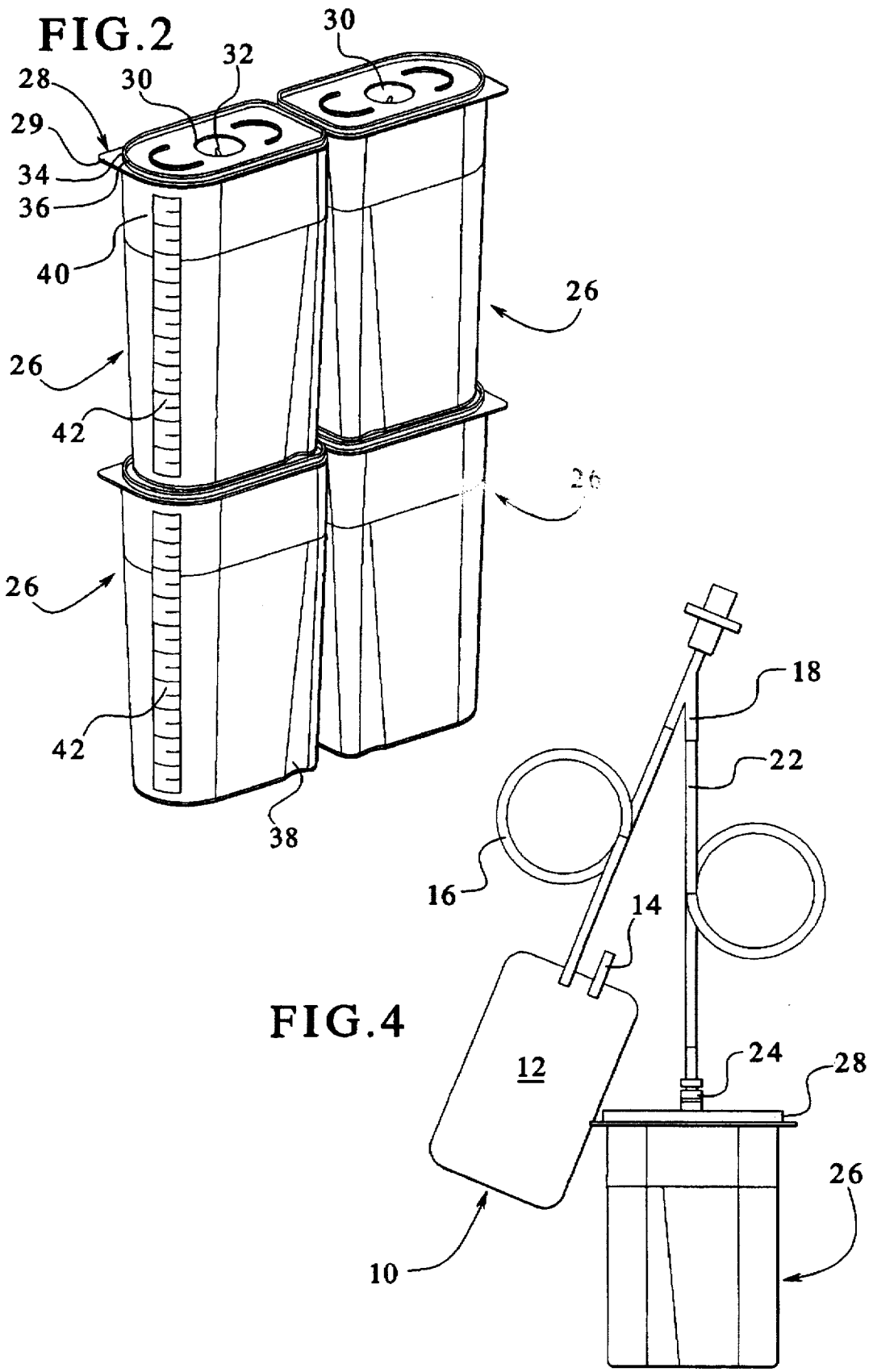

SOLUTION DELIVERY SYSTEM WITH INDIVIDUAL INTEGRATED FINAL PACKAGING AND A METHOD FOR PACKAGING THE SAME

BACKGROUND OF THE INVENTION

The present invention generally relates to a solution delivery system and a method for packaging the same. More specifically, the present invention relates to a solution delivery system used for continuous ambulatory peritoneal dialysis (CAPD) and a method for packaging the same. Still further, the present invention relates to a CAPD delivery system with integrated final packaging.

Typically, packaging for CAPD systems consists of a solution container, generally filled with peritoneal dialysis solution, which is linked, by means of a Y-set of tubing and a connector, to an empty drainage container. The drainage container is designed to receive at least one and one-half times the nominal fill volume of the solution container.

The entire CAPD system, i.e. the full bag, the Y-set and the empty bag, is wrapped in a pouch for storage prior to use by a patient. Typically, sterile products required for use with the CAPD system are delivered to the end users, such as patients requiring peritoneal dialysis. Often, the sterile products are packed in a corrugated carton box. As a result of the packaging currently used, a CAPD patient is required to open a carton, tear open an overpouch, and flatten one or more corrugated boxes each time a dialysis procedure is undertaken. Because many CAPD patients also suffer from arthritis, these tasks are often very difficult for the patient to perform.

Further, storage requirements of current systems prior to use is often burdensome due to the amount of space necessary with the type of packaging that is currently being used for storage. Namely, flexible overpouch packaging retains no specific shape; therefore, stacking of product is difficult. Further, identification of the product is also often difficult using the current system for packaging.

Another complex procedure using the current system is disposal of spent dialysis. With currently available systems, patients typically use scissors to cut off an end or corner, or drain line, or port tube of a filled, flexible drainage container in order to discard spent effluent. Further, after the product has been used, the amount of materials to be disposed is voluminous. An overpouch and a carton box must be discarded also requiring significant amounts of space.

Yet another drawback of the current system is that the packaging of the current system is not well protected and is prone to cosmetic defects, such as collapse of components, kinked tubing, sticking of components or torn components. Handling is, therefore, difficult since the packaging requires great care and, as a result, less automation may be implemented.

A need, therefore, exists for an improved system which can be integrated with the final packaging for use by a patient undergoing CAPD as well as an improved method for packaging and method for delivering a solution.

SUMMARY OF THE INVENTION

The present invention provides a CAPD delivery system with individual integrated final packaging. Further, the present invention provides a method for packaging a system for use by patients undergoing CAPD as well as a method for undergoing CAPD using a delivery system with integrated packaging.

To this end, in an embodiment, a solution delivery system is provided. The system has a rigid container having walls defining an interior wherein the rigid container has an open end and a closed end. A lid is attachable to the open end of the rigid container wherein the lid includes a port providing fluid communication with the interior of the rigid container. A container is filled with a solution having a length of tubing extending therefrom wherein the tubing is connectable, via a manifold and tubing, to the port on the lid.

In an embodiment, a connector is provided at an end of the length of tubing wherein the connector connects the tubing and the port on the lid.

In an embodiment, the container with the solution and the tubing are placed in the rigid container before attaching the lid.

In an embodiment, a connecting device is associated with the port on the lid.

In an embodiment, the walls of the rigid container are molded to form an indented section.

In an embodiment, the walls of the rigid container are tapered.

In an embodiment, a scale is incorporated on the wall of the rigid container. The scale may be printed or engraved.

In an embodiment, a transparent window is incorporated in the wall of the rigid container.

In an embodiment, the solution in the container is used for peritoneal dialysis.

In an embodiment, the rigid container is constructed from a recyclable material.

In an embodiment, the rigid container, the lid and/or the container are made of gas (carbon dioxide, oxygen, etc.) and water vapor barrier materials.

In an embodiment, the rigid container is constructed from a material including a bactericidal or bacterio-static agent.

In an embodiment, the lid is distinguishable in color from the rigid container.

In an embodiment, the lid and/or the rigid container include tactile features to allow differentiation by a blind or visually impaired patient, for example, of the solutions contained in the solution container.

In another embodiment of the present invention, a method is provided for packaging a system required for use in conducting a dialysis procedure. The method comprises the steps of: providing a first container having an interior defined by walls; providing a second container filled with the solution and connected to and in fluid communication with a length of tubing; placing the second container and the length of tubing in a first container; and enclosing the first container with a lid.

In an embodiment, the method further comprises the step of providing an access port in the lid enclosing the first container.

In an embodiment, the method further comprises the step of forming the first container such that at least one of the walls of the first container is designed for gripping.

In an embodiment, the first container is constructed from a rigid material.

In an embodiment, the method further comprises the steps of: providing a third container having a lid for enclosing an interior of the third container; and stacking the third container on the lid of the first container.

In an embodiment, the method further comprises the step of providing a scale on the walls of the first container.

In an embodiment, the method further comprises the step of providing a window incorporated with the walls of the first container.

In an embodiment, the method further comprises the step of forming the first container with a semi-circular corner at an open end on which the lid is secured to enclose the first container. The lid, in an embodiment, may include a section that is openable and resealable to allow for emptying of the first container.

In another embodiment of the present invention, a method is provided for delivering a solution to a patient. The method comprises the steps of: providing a first container having walls defining an interior, the first container having a lid wherein the lid includes an access port to provide access to the interior of the first container; connecting a first length of tubing to the access port and lid; providing a second container holding a solution; connecting a second length of tubing to the second container at one end and to the patient at its other end; and allowing the solution to flow from the second container to the patient.

In an embodiment, the method further comprises the step of connecting the first length of tubing to the second length of tubing.

In an embodiment, the method further comprises the step of draining solution from the container through the first length of tubing to the first container.

In an embodiment, the method further comprises the step of monitoring fill of the first container during draining from the patient.

In an embodiment, the first container is constructed from a rigid material.

It is, therefore, an advantage of the present invention to provide a system and a method that simplifies continuous ambulatory peritoneal dialysis (CAPD).

Another advantage of the present invention is to provide a system and a method for packaging products required for CAPD.

A still further advantage of the present invention is to provide a system and a method in which a portion of the packaging is used for CAPD.

Yet another advantage of the present invention is to provide a system and a method that simplifies use for a patient undergoing CAPD.

A still further advantage of the present invention is to provide a system and a method that eases storage and identification of a CAPD product.

And, another advantage of the present invention is to provide a system and a method for packaging a system for CAPD that is stackable before and after use.

Moreover, an advantage of the present invention is to provide a system and a method for packaging a product used for CAPD wherein the product is readily identifiable.

Yet another advantage of the present invention is to provide a system and a method for packaging a CAPD product that simplifies use through controlling and monitoring drain fluid volume during a drainage phase of the procedure.

Further, an advantage of the present invention is to provide a system and a method for packaging a CAPD system that is clean, and that easily and quickly disposes of the spent effluent following a fluid exchange.

A still further advantage of the present invention is to provide a system and a method for packaging a CAPD system wherein the product is protected and not prone to cosmetic defects.

And, another advantage of the present invention is to provide a system and a method for packaging a CAPD product wherein handling of the product may be automated and simplified.

A still further advantage of the present invention is to provide a system and a method for packaging components required for CAPD that reduces the amount of material that must be disposed.

Yet another advantage of the present invention is to provide a system and a method for packaging components required for CAPD that reduces the time required to perform an exchange.

Additional features and advantages of the present invention are described in, and will be apparent from, the detailed description of the presently preferred embodiments and from the drawings.

BRIEF DESCRIPTION OF THE DRAWINGS

FIG. 1 illustrates a schematic diagram of an embodiment of components necessary for performing a dialysis procedure using packaging of the present invention.

FIG. 2 illustrates a perspective view of a plurality of packaged sets as used in a dialysis procedure with the present invention.

FIG. 3 illustrates a perspective view, partially in cross-section, of an embodiment of the components necessary for performing a dialysis procedure within a rigid container.

FIG. 4 illustrates a side elevational view of the components necessary for performing a dialysis procedure connected to a rigid container in an embodiment of the present invention.

DETAILED DESCRIPTION OF THE PRESENTLY PREFERRED EMBODIMENTS

The present invention provides a system and a method for packaging. More specifically, the present invention provides a system and a method for packaging components required to conduct a dialysis procedure, such as continuous ambulatory peritoneal dialysis (CAPD).

Referring now to the drawings wherein like numerals refer to like parts, FIG. 1 illustrates an embodiment of a system 1 of components necessary for conducting CAPD using the packaging of the present invention to be hereinafter described with reference to the remaining Figures. In FIG. 1, a container 10 is shown. The container 10 is typically made of a flexible plastic and contains a volume of solution 12 therein. The material from which the container 10 is constructed may also provide a barrier to gas, light and water vapor to allow for a sufficient shelf life of the solution 12 therein and to also prevent solution degradation during the shelf life due to light or gas permeation. Of course, other materials for the container 10 may be implemented by those skilled in the art. The container 10 is connected to a medication access port 14 which may selectively add medication to the solution 12 in the container 10.

Alternatively, the solution 12 within the container may be drawn from the container 10 via the medication access port 14. The interior of the container 10 containing the solution 12 is also in fluid communication with an administration line 16. The administration line 16 connects to a manifold junction 18, such as a Y-connector as illustrated in FIG. 1. Within the manifold junction 18 is a valve closure 20 that controls administration of solution to and from a patient using the system 1. The valve closure 20 is connected to the manifold junction 18. Preferably, the valve closure 20 is sealed by a cover or protector (not shown) to maintain sterility of the system 1. A drainage line 22 is connected to an opposite leg of the manifold junction 18 and is, in turn, connected at its end to a drain line closure/connector 24. The manifold junction 18 may also allow for linking a plurality of solution containing bags to the drain line 22. Of course, clamping devices and other accessories may be added to the system 1, such as an on-line medication port, on-line valving, a multiple branch manifold, etc.

Referring now to FIG. 2, a plurality of rigid containers 26 are illustrated in a side-by-side and stacked orientation. The rigid containers 26 are specifically designed with a tapered exterior wall such that the base of one rigid container 26 may stand on a lid 28 of an adjacent rigid container 26. Also, the tapered walls allows rigid containers 26 to be stacked one within another when the lids 28 are removed from the rigid containers 26. Alternatively, the rigid container 26 may be designed and/or constructed so as to be collapsible. The materials of the container 26 could be either rigid or semi-rigid, and/or the design of the container 26 may be such that, for example, weak sections may collapse under a sufficient load.

As illustrated, the lids 28 of each of the rigid containers 26 include an access port 30 through which selective fluid communication with an interior of the rigid container 26 can be achieved. Through the center of the access port 30 is a connecting device 32, such as a rigid spike. The connecting device 32 is used to pierce the drain line closure/connector 24 of the system 1. The lid 28 further includes a seal 34 within an interior of a recessed area 36 for receiving an end of the rigid container 26. The seal 34 of the lid 28 realizes a leakproof, non-permanent seal for the rigid container 26. The lid 28 also includes a rim 29 to assist in removal of the lid 28 from the rigid container 26.

The rigid container 26 is designed with an integrated prehension means or handle 38 along two exterior sides of the rigid container 26. The handle 38 may be designed as an indented, molded area of the rigid container 26 which allows an individual to grip the rigid container 26 and maneuver the same as desired. One end 40 of the rigid container 26 is substantially semi-circular at the end opposite the handle 38. The semi-circular shape of the end 40 provides an integrated means for pouring solution from the rigid container 26.

The rigid container 26 may also include a graduated scale 42. The scale 42 may be molded in a wall of the rigid container 26 or may be otherwise printed on the rigid container 26 in a known manner such that solution as it is being filled within the interior of the rigid container 26 can at least partially be seen through the walls of the rigid container 26 and the amount of solution within the rigid container 26 may be read from the scale 42. Alternatively, the rigid container 26 may include a window, either transparent or translucent, through which the solution or labeling of the solution container 10 may be viewed. The transparent window may also include its own graduated scale to indicate amount of solution within the rigid container 26.

The rigid container 26, although described as rigid, may be constructed from a rigid or semi-rigid material. The material of the rigid container 26 may be selected so as to guarantee the shelf-life of the CAPD product within the bucket, i.e. low water vapor transmission rate material. Alternatively, the material may also be selected to guarantee the integrity of the CAPD solution, i.e. gas barrier material and/or light barrier material. A selected blend of raw material for the rigid container 26 may also be selected to prevent mold growth during the shelf-life of the CAPD product. Further, a selected material may also enable multiple uses of the same bucket. To this end, the bucket may include a material containing a bactericidal or bacterio-static agent.

While the lid 28 has been described to include the access port 30 having the connecting device 32, the access port 30 may, alternatively, include a membrane, a luer lock system, a split septum, or the like that can be used in conjunction with the drain line closure/connector 24. The lid 28 also includes micro-perforations (not shown) to allow venting of the closed drainage container without jeopardizing the water tightness of the assembled rigid container 26 and lid 28.

A dust protector tab (not shown) may also be provided to cover the access port 30 and, if needed, the micro-perforations included in the lid 28 to avoid collecting any contaminants, to avoid spillage, or the like. The material of the lid 28, like the rigid container 26, may also be selected to guarantee the integrity of the CAPD solution and may be selected to prevent mold growth over the shelf-life of the CAPD product. Further, the lid 28 and/or the rigid container 26 may be color coded to differentiate between different products for which the rigid container 26 and associated components may be used.

Preferably, the rigid container 26 and the lid 28 are injection molded; however, the individual integrated final packaging can be obtained out of a thermal forming manufacturing process as well. Alternatively, the individual integrated final packaging can also be obtained from a blow molding manufacturing process.

Still further, instead of preventing mold growth using a specified blend of materials for the rigid container 26 and the lid 28, the volume determined by the rigid container 26 and the lid 28 could be flushed with a sufficient amount of an antibacterial gas through an appropriate access port constitutive of a re-sealable valve, i.e. split septum, over-molded elastomeric access, etc., or the bucket could also contain a specified amount of liquid disinfectant, such as hypochlorite or the like. Still further, a tablet containing active disinfectant could also be placed in the bucket. Water vapor would then release the active disinfectant in the enclosed volume determined by the rigid container 26 and the lid 28.

Referring now to FIG. 3, the rigid container 26 is illustrated, partially cut away wherein the system 1 shown in FIG. 1 may be entirely placed within the rigid container 26 and enclosed by the lid 28 for shipment and storage of the same. As a result, the system 1 including the container 10 filled with solution 12 is protected from cosmetic defects, such as damage due to accidental piercing of the container 10, or the like.

In use, the system 1 is removed from the rigid container 26 and connected as illustrated in FIG. 4 such that the drain line closure/connector 24 is connected to the access port 30 in the lid 28 of the rigid container 26. Via the connector 15 of the system 1, a length of tubing (not shown) can be connected to provide fluid communication between the system 1 and a point of delivery, such as a patient undergoing peritoneal dialysis. As a result, the peritoneum of the patient may be drained through the length of tubing leading to the patient, the connector 15, the drainage line 22, the drain line closure/connector 24 and then ultimately drains into the rigid container 26. Following this procedure, the solution 12 from the container 10 may be drained through the administration line 16 through the manifold junction 18 and the connector 15 into the length of tubing to the patient. The amount of solution being drained into the rigid container 26 can be monitored via the scale 42 (or scaled window) on an exterior wall of the rigid container. After the drain and infusion procedures are complete, the solution within the rigid container 26 may be emptied by removing the lid 28 from the rigid container 26 and pouring the solution using the handle 28 and the spouted end 40 from the rigid container 26. In the latter case, the rigid container 26 may then be re-used for subsequent procedures by merely replacing the system 1 in the rigid container 26.

Although the present invention has been described with reference to a peritoneal dialysis procedure, it should be understood that the present invention is adaptable to other fluid control systems, such as intravenous feeding.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A solution delivery system comprising:

a rigid container having walls defining an interior wherein the rigid container has an open end and a closed end;

a lid attachable to the open end of the rigid container wherein the lid includes a port providing fluid communication with the interior of the rigid container; and a container having an interior filled with a solution having a length of tubing extending therefrom wherein the tubing is connectable to the port on the lid.

2. The system of claim 1 further comprising:

a connector at an end of the length of tubing wherein the connector connects the tubing and the port on the lid.

3. The system of claim 1 wherein the container with the solution and the tubing are placed in the rigid container before closing the rigid container with the lid.

4. The system of claim 1 further comprising:

a connecting device associated with the port on the lid.

5. The system of claim 1 wherein the walls of the rigid container are molded to form an indented section.

6. The system of claim 1 wherein the walls of the rigid container are tapered.

7. The system of claim 1 further comprising:

a scale incorporated on the wall of the rigid container.

8. The system of claim 7 wherein the scale is printed.

9. The system of claim 7 wherein the scale is engraved.

10. The system of claim 1 further comprising:

a transparent window incorporated in the wall of the rigid container.

11. The system of claim 1 wherein the solution in the container is used for peritoneal dialysis.

12. The system of claim 1 wherein the rigid container is constructed from a recyclable material.

13. The system of claim 1 wherein the rigid container is constructed from a material including bactericidal or bacterio-static agent.

14. The system of claim 1 wherein the lid is distinguishable in color from the rigid container.

15. A method for packaging a system required for use in conducting a dialysis procedure, the method comprising the steps of:

providing a first container having an interior defined by walls;

providing a second container filled with solution and connected to and in fluid communication with a length of tubing;

placing the second container and the length of tubing in the first container; and enclosing the first container with a lid.

16. The method of claim 15 further comprising the step of:

providing an access port in the lid enclosing the first container.

17. The method of claim 15 further comprising the step of:

forming the first container such that at least one of the walls of the first container is designed for gripping.

18. The method of claim 15 wherein the first container is constructed from a rigid material.

19. The method of claim 15 further comprising the steps of:

providing a third container having a lid for enclosing an interior of the third container; and stacking the third container on the lid of the first container.

20. The method of claim 15 further comprising the step of:

providing a scale on the walls of the first container.

21. The method of claim 15 further comprising the step of:

providing a window incorporated with the walls of the first container.

22. The method of claim 15 further comprising the step of:

forming the first container with a semi-circular corner at an open end on which the lid is secured to enclose the first container.

23. A method for delivering a solution to a patient, the method comprising the steps of:

providing a first container having walls defining an interior, the first container having a lid wherein the lid includes an access port to provide access to the interior of the first container;

connecting a first length of tubing to the access port in the lid;

providing a second container holding a solution; connecting a second length of tubing to the second container at one end and to the patient at its other end; and allowing the solution to flow from the second container to the patient.

24. The method of claim 23 further comprising the step of:

connecting the first length of tubing to the second length of tubing.

25. The method of claim 23 further comprising the step of:

draining solution from the patient through the first length of tubing to the first container.

26. The method of claim 23 further comprising the step of:

monitoring fill of the first container during draining from the patient.

27. The method of claim 23 wherein the first container is constructed from a rigid material.

* * * * *